(12) United States Patent
Obokata et al.

(10) Patent No.: US 6,558,906 B2
(45) Date of Patent: May 6, 2003

(54) METHODS OF SCREENING POTENTIAL TRANSLATIONAL REGULATORY ELEMENTS OF MESSENGER RNA

(75) Inventors: Junichi Obokata, Aichi (JP); Issei Nagao, Hokkaido (JP)

(73) Assignees: Toyota Jidosha Kabushiki Kaisha (JP); Genesis Research Institute, Incorporated (JP)

( * ) Notice: Subject to any disclaimer, the term of this patent is extended or adjusted under 35 U.S.C. 154(b) by 0 days.

(21) Appl. No.: 09/816,089

(22) Filed: Mar. 26, 2001

(65) Prior Publication Data

US 2002/0086299 A1 Jul. 4, 2002

(30) Foreign Application Priority Data

Sep. 25, 2000 (JP) ........................................ 2000/291084

(51) Int. Cl.$^7$ .......................... C12Q 1/68; C12N 15/00; C07H 21/02; C07H 21/04
(52) U.S. Cl. .......................... 435/6; 435/440; 536/23.1; 536/24.3
(58) Field of Search .................... 435/6, 440; 536/23.1, 536/24.3

(56) References Cited

U.S. PATENT DOCUMENTS

| | | | |
|---|---|---|---|
| 5,489,527 A | * | 2/1996 | Wilson |
| 5,648,235 A | * | 7/1997 | Zurr et al. |
| 5,658,754 A | * | 8/1997 | Kawasaki |
| 5,981,177 A | * | 11/1999 | Demirjian et al. |
| 6,187,564 B1 | * | 2/2001 | Sytkowski |

OTHER PUBLICATIONS

Hirama et al., Analytical Biochemistry 155 : 385–390 (1986).*
Daniel R, Gallie and M. Kobayashi, Gene 1994, 142:159–165.
Y. Yamamoto et al., The Journal of Biological Chemistry, 1995, 279(21):12466–12470.
Julia Bailey–Serres, Elsevier Science 1999, 4(4):142–148.
A–C Gingras et al., Annual Reviews Biochem. 1999, 68:913–963.
Ellie Ehrenfeld, Translational Control 1996, Initiation of Translation by Picornavirus RNAs, Cold Spring Harbor Laboratory Press, pp 549–573.

\* cited by examiner

Primary Examiner—Ethan C. Whisenant
(74) Attorney, Agent, or Firm—Kenyon & Kenyon

(57) ABSTRACT

The present invention relates to a method of screening a potential translational regulatory element of mRNA, which promotes or suppresses the translation efficiency of mRNA in a given translation system, by applying the in vitro evolution principles. Specifically, the present invention relates to a method of screening a potential translational regulatory element of mRNA, comprising the steps of synthesizing mRNAs with random oligonucleotide sequences, which are candidates of translational regulatory elements, introduced into the untranslated regions (UTRs), and selecting mRNAs with altered translation efficiency by virtue of the inserted motifs; to translational regulatory elements screened by this method; and to a method of isolating mRNA with altered translation efficiency in comparison with the native mRNA by using such a screening method.

12 Claims, 4 Drawing Sheets

SEQUENCE LISTING

<160> NUMBER OF SEQ ID NOS: 28

<210> SEQ ID NO 1
<211> LENGTH: 94
<212> TYPE: DNA
<213> ORGANISM: Artificial Sequence
<220> FEATURE:
<223> OTHER INFORMATION: Primer
<221> NAME/KEY: misc_feature
<222> LOCATION: 50, 51, 52, 53, 54, 55, 56, 57, 58, 59, 60, 61, 62, 63, 64
<223> OTHER INFORMATION: n = A,T,C or G

<400> SEQUENCE: 1
gcaggcctaa tacgactcac tatagggccg ctctagaact agtggatccn nnnnnnnnn     60 nnnnatgtta cgtcctgtag aaaccccaac ccgt                                94

```
<210> SEQ ID NO 2
<211> LENGTH: 90
<212> TYPE: DNA
<213> ORGANISM: Artificial Sequence
<220> FEATURE:
<223> OTHER INFORMATION: Primer

<400> SEQUENCE: 2
tttttttttt tttttttttt tttttttttt tttttttttt tttttttttt cgagctcgag      60
attcacactt cctgattatt gacccacact                                       90

<210> SEQ ID NO 3
<211> LENGTH: 63
<212> TYPE: DNA
<213> ORGANISM: Artificial Sequence
<220> FEATURE:
<223> OTHER INFORMATION: Primer

<400> SEQUENCE: 3
gcctgcaggg cctaatacga ctcactatag ggatccctta tgttacgtcc tgtagaaacc      60
cca                                                                    63

<210> SEQ ID NO 4
<211> LENGTH: 67
<212> TYPE: DNA
<213> ORGANISM: Artificial Sequence
<220> FEATURE:
<223> OTHER INFORMATION: Primer
<221> NAME/KEY: misc_feature
<222> LOCATION: 22, 23, 24, 25, 26, 27, 28, 29, 30, 31, 32, 33, 34, 35,
      36
<223> OTHER INFORMATION: n = A,T,C or G

<400> SEQUENCE: 4
ccctcgaggt cgacggtatc gnnnnnnnnn nnnnnngagc tcgagattca cacttcctga      60
ttattga                                                                67

<210> SEQ ID NO 5
<211> LENGTH: 71
<212> TYPE: DNA
<213> ORGANISM: Artificial Sequence
<220> FEATURE:
<223> OTHER INFORMATION: Primer

<400> SEQUENCE: 5
tttttttttt tttttttttt tttttttttt tttttttttt tttttttttt ccctcgaggt      60
cgacggtatc g                                                           71

<210> SEQ ID NO 6
<211> LENGTH: 48
<212> TYPE: DNA
<213> ORGANISM: Artificial Sequence
<220> FEATURE:
<223> OTHER INFORMATION: Primer

<400> SEQUENCE: 6
gcaggcctaa tacgactcac tatagggccg ctctagaact agtggatc                   48

<210> SEQ ID NO 7
<211> LENGTH: 59
<212> TYPE: DNA
<213> ORGANISM: Artificial Sequence
<220> FEATURE:
```

<223> OTHER INFORMATION: Primer

<400> SEQUENCE: 7
gcaggcctaa tacgactcac tatagggatc caaatggaag acgccaaaaa cataaagaa        59

<210> SEQ ID NO 8
<211> LENGTH: 93
<212> TYPE: DNA
<213> ORGANISM: Artificial Sequence
<220> FEATURE:
<223> OTHER INFORMATION: Primer

<400> SEQUENCE: 8
tttttttttt tttttttttt tttttttttt tttttttttt tttttttttt cgagctcgag        60
attttagttc gcgggcgcaa ctgcaactcc gat                                    93

<210> SEQ ID NO 9
<211> LENGTH: 15
<212> TYPE: DNA
<213> ORGANISM: Artificial Sequence
<220> FEATURE:
<223> OTHER INFORMATION: Primer

<400> SEQUENCE: 9
agguugcaua uuccg                                                         15

<210> SEQ ID NO 10
<211> LENGTH: 15
<212> TYPE: DNA
<213> ORGANISM: Artificial Sequence
<220> FEATURE:
<223> OTHER INFORMATION: Primer

<400> SEQUENCE: 10
ucuauugguu ucaac                                                         15

<210> SEQ ID NO 11
<211> LENGTH: 15
<212> TYPE: DNA
<213> ORGANISM: Artificial Sequence
<220> FEATURE:
<223> OTHER INFORMATION: Primer

<400> SEQUENCE: 11
uagauauccg cgcuu                                                         15

<210> SEQ ID NO 12
<211> LENGTH: 15
<212> TYPE: DNA
<213> ORGANISM: Artificial Sequence
<220> FEATURE:
<223> OTHER INFORMATION: Primer

<400> SEQUENCE: 12
auacucgcgu uauca                                                         15

<210> SEQ ID NO 13
<211> LENGTH: 15
<212> TYPE: DNA
<213> ORGANISM: Artificial Sequence
<220> FEATURE:
<223> OTHER INFORMATION: Primer

<400> SEQUENCE: 13
acagugccua auccu                                                         15

```
<210> SEQ ID NO 14
<211> LENGTH: 15
<212> TYPE: DNA
<213> ORGANISM: Artificial Sequence
<220> FEATURE:
<223> OTHER INFORMATION: Primer

<400> SEQUENCE: 14
acugcaaguc cgcuc                                                    15

<210> SEQ ID NO 15
<211> LENGTH: 15
<212> TYPE: DNA
<213> ORGANISM: Artificial Sequence
<220> FEATURE:
<223> OTHER INFORMATION: Primer

<400> SEQUENCE: 15
gcauauuagc accgc                                                    15

<210> SEQ ID NO 16
<211> LENGTH: 15
<212> TYPE: DNA
<213> ORGANISM: Artificial Sequence
<220> FEATURE:
<223> OTHER INFORMATION: Primer

<400> SEQUENCE: 16
gagcugccag guugc                                                    15

<210> SEQ ID NO 17
<211> LENGTH: 14
<212> TYPE: DNA
<213> ORGANISM: Artificial Sequence
<220> FEATURE:
<223> OTHER INFORMATION: Primer

<400> SEQUENCE: 17
aguaccauac ucuu                                                     14

<210> SEQ ID NO 18
<211> LENGTH: 15
<212> TYPE: DNA
<213> ORGANISM: Artificial Sequence
<220> FEATURE:
<223> OTHER INFORMATION: Primer

<400> SEQUENCE: 18
aaccuuugcu uucgc                                                    15

<210> SEQ ID NO 19
<211> LENGTH: 15
<212> TYPE: DNA
<213> ORGANISM: Artificial Sequence
<220> FEATURE:
<223> OTHER INFORMATION: Primer

<400> SEQUENCE: 19
uacuuauauc uccaa                                                    15

<210> SEQ ID NO 20
<211> LENGTH: 15
<212> TYPE: DNA
<213> ORGANISM: Artificial Sequence
<220> FEATURE:
```

```
<223> OTHER INFORMATION: Primer

<400> SEQUENCE: 20
guacccacgg cguua                                                    15

<210> SEQ ID NO 21
<211> LENGTH: 15
<212> TYPE: DNA
<213> ORGANISM: Artificial Sequence
<220> FEATURE:
<223> OTHER INFORMATION: Primer

<400> SEQUENCE: 21
aacuacuuac cuuaa                                                    15

<210> SEQ ID NO 22
<211> LENGTH: 15
<212> TYPE: DNA
<213> ORGANISM: Artificial Sequence
<220> FEATURE:
<223> OTHER INFORMATION: Primer

<400> SEQUENCE: 22
cacaagccgc cuuaa                                                    15

<210> SEQ ID NO 23
<211> LENGTH: 15
<212> TYPE: DNA
<213> ORGANISM: Artificial Sequence
<220> FEATURE:
<223> OTHER INFORMATION: Primer

<400> SEQUENCE: 23
uugucgguug uccau                                                    15

<210> SEQ ID NO 24
<211> LENGTH: 15
<212> TYPE: DNA
<213> ORGANISM: Artificial Sequence
<220> FEATURE:
<223> OTHER INFORMATION: Primer

<400> SEQUENCE: 24
ucuggauacu cucug                                                    15

<210> SEQ ID NO 25
<211> LENGTH: 15
<212> TYPE: DNA
<213> ORGANISM: Artificial Sequence
<220> FEATURE:
<223> OTHER INFORMATION: Primer

<400> SEQUENCE: 25
auacacuguc cuaua                                                    15

<210> SEQ ID NO 26
<211> LENGTH: 15
<212> TYPE: DNA
<213> ORGANISM: Artificial Sequence
<220> FEATURE:
<223> OTHER INFORMATION: Primer

<400> SEQUENCE: 26
ccagauauaa ccaca                                                    15
```

-continued

```
<210> SEQ ID NO 27
<211> LENGTH: 15
<212> TYPE: DNA
<213> ORGANISM: Artificial Sequence
<220> FEATURE:
<223> OTHER INFORMATION: Primer

<400> SEQUENCE: 27
uuuucacacu cgccu                                                    15

<210> SEQ ID NO 28
<211> LENGTH: 15
<212> TYPE: DNA
<213> ORGANISM: Artificial Sequence
<220> FEATURE:
<223> OTHER INFORMATION: Primer

<400> SEQUENCE: 28
gcgaugauac uuugc                                                    15
```

US 6,558,906 B2

METHODS OF SCREENING POTENTIAL TRANSLATIONAL REGULATORY ELEMENTS OF MESSENGER RNA

FIELD OF THE INVENTION

The present invention relates to a method of screening potential translational regulatory elements of mRNAs. More specifically, it relates to the method comprising the steps of synthesizing mRNAs which comprise candidates of translational regulatory elements introduced into the untranslated regions (UTRs), and selecting mRNAs with altered translation efficiency by virtue of the inserted motifs.

The present invention also relates to translational regulatory elements screened by the above-described method.

The present invention further relates to a method of isolating a mRNA with altered translation efficiency in comparison with native mRNA by using the above-described method.

BACKGROUND OF THE INVENTION

It is known that an element, which is present in the 5'-UTR or 3'-UTR of mRNA to control a translation efficiency of the mRNA, plays an important role in regulation of gene expression (Gallie, D. R. and Kobayashi, M., 1994, Gene, 142: 159–165; Yamamoto, Y. et al., 1995, J. Biol. Chem., 270: 12466–12470; Bailey-Serres, J., 1999, Trends Plant Sci., 4: 142–148). The UTR motif is thought to affect a translational initiation frequency by various molecular mechanisms. However, so far there have been known only few examples of analysis for a relation of UTR and translational initiation frequency, and this relation still remains unknown for most genes. In the UTRs there may probably exist various unknown translational regulatory motifs as well as control mechanisms mediated by these motifs. Moreover, there is no example that common properties, motifs, or structures were found among known translational regulatory elements. If there are methods for systematically screening translational regulatory motifs which function in the UTRs, it would enable to clarify basic characteristics of the function essential for the regulatory motifs, or to establish technology to precisely control the expression of a gene of interest at its translation level.

Under the circumstances, the object of this invention is to provide a method of screening potential translational regulatory elements that promote or suppress the translation efficiency of given mRNAs in a translation system, by applying the principles of in vitro evolution.

SUMMARY OF THE INVENTION

The inventors have now found a procedure to isolate and analyze a group of UTR regulatory sequences functioning in a given translation system by using an in vitro evolution system of a model gene instead of analyzing UTRs of individual genes one by one. That is, the procedure involves the steps of introducing random nucleotide sequences into UTRs which are potential regulatory sites for gene expression, and repeating the screening of mRNAs that become preferentially translated, or untranslated, in a given translation system due to an effect of the inserted sequence.

Accordingly, the present invention is summarized as follows.

In one aspect of the present invention, the invention provides a method of screening a potential translational regulatory element of mRNA, comprising the steps of synthesizing mRNAs containing random oligonucleotide sequences, which are candidates of translational regulatory elements, introduced into the untranslated regions (UTRs), and selecting mRNA with altered translation efficiency by virtue of the inserted motifs.

In one embodiment of the invention, the selection of the mRNA comprises: (a) introducing a mRNA population, which contains various translational regulatory motif candidates in the UTRs, into an in vitro or in vivo translation system to produce polysomes; and (b) separating a polysomal mRNA with altered translation efficiency.

In another embodiment of the invention, the selection of the mRNA further comprises: (c) extracting RNA from the separated polysomes; and (d) synthesizing a DNA fragment with the RNA as a template, then synthesizing a mRNA with the DNA fragment as a template.

In further embodiment of the invention, the selection of the mRNA further comprises: (e) repeating at least once said steps (a) to (d) for the synthesized mRNA to isolate substantially pure mRNA with altered translation efficiency; and (f) determining a sequence of a potential translational regulatory element introduced into the isolated mRNA.

In further embodiment of the invention, the mRNA synthesized contains either of a Cap structure or a Poly(A) strand, or both. That is, the mRNA is: (1) mRNA containing a Cap structure and a Poly (A) strand, (2) mRNA containing a Cap structure but containing no Poly (A) strand, or (3) mRNA containing no Cap structure but containing a Poly (A) strand. The term "Poly (A)" as used herein means polyadenylic acid. The Cap structure is present at the 5'-end of mRNA of a eukaryotic cell or viruse, and it is involved in the initiation reaction for protein synthesis and the like.

In further embodiment of the invention, the in vitro translation system is a cell-free protein synthesis system, and the in vivo translation system is an eukaryotic cell.

In further embodiment of the invention, the separation of polysomes in the step (b) is performed based on the size of polysomes.

In further embodiment of the invention, the mRNA with altered translation efficiency has a higher or lower translation efficiency than that of native mRNA, preferably higher translation efficiency.

Examples of the method of screening according to this invention are as follows:

(1) a method of screening a potential translational regulatory element of mRNA, comprising the steps of:

(a) synthesizing mRNAs containing random oligonucleotide sequences, which are candidates of translational regulatory elements, introduced into the untranslated regions (or UTRs);

(b) introducing the mRNA population synthesized in step (a), which contains various translational regulatory motif candidates in the UTRs, into an in vitro or in vivo translation system to produce polysomes;

(c) separating, based on size, a polysome containing mRNA which has an altered translation efficiency;

(d) extracting RNA from the polysome separated in step (c);

(e) synthesizing a DNA fragment using the RNA extracted in step (d) as a template, then mRNA using the DNA fragment as a template;

(f) repeating at least once the steps (b) to (e) for the mRNA obtained in step (e), and then isolating substantially pure mRNA with altered translation efficiency; and (g) determining a sequence of a potential translational regulatory element introduced in the mRNA isolated in step (f).

(2) A method of screening a potential translational regulatory element of mRNA, which comprises the steps of:

(a) synthesizing mRNAs containing random oligonucleotide sequences, which are candidates of translational regulatory elements, introduced in the 5'-untranslated region (5'-UTR), and containing a Cap structure and a Poly (A) strand sequence;

(b) introducing the mRNA population synthesized in step (a), which contains various translational regulatory motif candidates in the 5'-UTR, into an in vitro or in vivo translation system to produce polysomes;

(c) separating, based on size, a polysome containing mRNA which has a translation efficiency higher than that of the native mRNA;

(d) extracting RNA from the polysome separated in step (c);

(e) synthesizing a DNA fragment using the RNA extracted in step (d) as a template, then mRNA using the DNA fragment as a template;

(f) repeating at least once the steps (b) to (e) for the mRNA obtained in step (e), and then isolating substantially pure mRNA with translation efficiency higher or lower than that of the native mRNA; and (g) determining a sequence of a potential translational regulatory element introduced in the mRNA isolated in step (f).

(3) A method of screening a potential translational regulatory element of an mRNA, which comprises the steps of:

(a) synthesizing mRNAs containing random oligonucleotide sequences, which are candidates of translational regulatory elements, introduced in the 3'-untranslated region (3'-UTR), and containing no Cap structure but a Poly (A) stand sequence;

(b) introducing the mRNA population, synthesized in step (a), which contains various translation-regulating sequence candidates in the 3'-UTR, into an in vitro or in vivo translation system to produce polysomes;

(c) separating, based on size, a polysome containing the mRNA which has a translation efficiency higher than the native mRNA;

(d) extracting RNA from the polysome separated in step (c);

(e) synthesizing a DNA fragment using the RNA extracted in step (d) as a template, then mRNA using the DNA fragment as a template;

(f) repeating at least once the steps (b) to (e) for the mRNA obtained in step (e), and then isolating substantially pure mRNA with translation efficiency higher or lower than that of the native mRNA; and (g) determining a sequence of a potential translational regulatory element introduced into the mRNA isolated in step (f).

In another aspect of the present invention, the invention provides a method of screening a translational regulatory element of a native mRNA with high translation efficiency, comprising the steps of:

(a) introducing a mRNA population, which contains various translational regulatory motifs in either or both of the untranslated regions, into an in vitro or in vivo translation system to produce polysomes;

(b) separating based on the size a polysome containing the mRNA which has a high translation efficiency;

(c) extracting an mRNA from the polysome separated in step (b);

(d) synthesizing a DNA fragment using the RNA extracted in step (c) as a template, then mRNA using the DNA fragment as a template;

(e) repeating at least once the steps (a) to (d) for the mRNA obtained in step (d), and then isolating substantially pure mRNA with high translation efficiency; and (f) determining a sequence of a translational regulatory element of the mRNA isolated in step (e).

The present invention, in further aspect thereof, provides a translational regulatory element comprising a sequence selected from the group consisting of sequences represented by SEQ ID NOS: 9 to 28.

In yet another aspect, the present invention provides a method of isolating an mRNA with altered translation efficiency in comparison with natural (or native or intact) mRNA by using any one of the methods as described above. Specifically, the method comprises the steps of:

(a) synthesizing mRNAs containing random oligonucleotide sequences, which are candidates of translational regulatory elements, introduced into the untranslated regions (or UTRs);

(b) introducing the mRNA population synthesized in step (a), which contains various translational regulatory motif candidates in the UTRs, into an in vitro or in vivo translation system to produce polysomes;

(c) separating, based on size, a polysome containing mRNA which has an altered translation efficiency;

(d) extracting RNA from the polysome separated in step (c);

(e) synthesizing a DNA fragment using the RNA extracted in step (d) as a template, then mRNA using the DNA fragment as a template; and (f) repeating at least once the steps (b) to (e) for the mRNA synthesized in step (e), and then isolating substantially pure mRNA with altered translation efficiency.

The mRNA of the step (a) above can contain either a Cap structure or a Poly(A) strand, or both.

BRIEF DESCRIPTION OF THE DRAWINGS

FIG. 3 shows changes in translational activity with enrichment cycles.

FIG. 4 shows the sequences and translational activities of translation-promoting elements of mRNA populations whose translation was promoted.

DETAILED DESCRIPTION OF THE INVENTION

More detailed explanation will be given for the method of this invention.

This method comprises the steps of synthesizing mRNA containing random oligonucleotide sequences, which are translational regulatory element candidates, introduced into the untranslated regions (or UTRs), and selecting mRNA with altered translation efficiency by virtue of the inserted motifs.

For example, the mRNA can be synthesized as follows.

Figure 1:
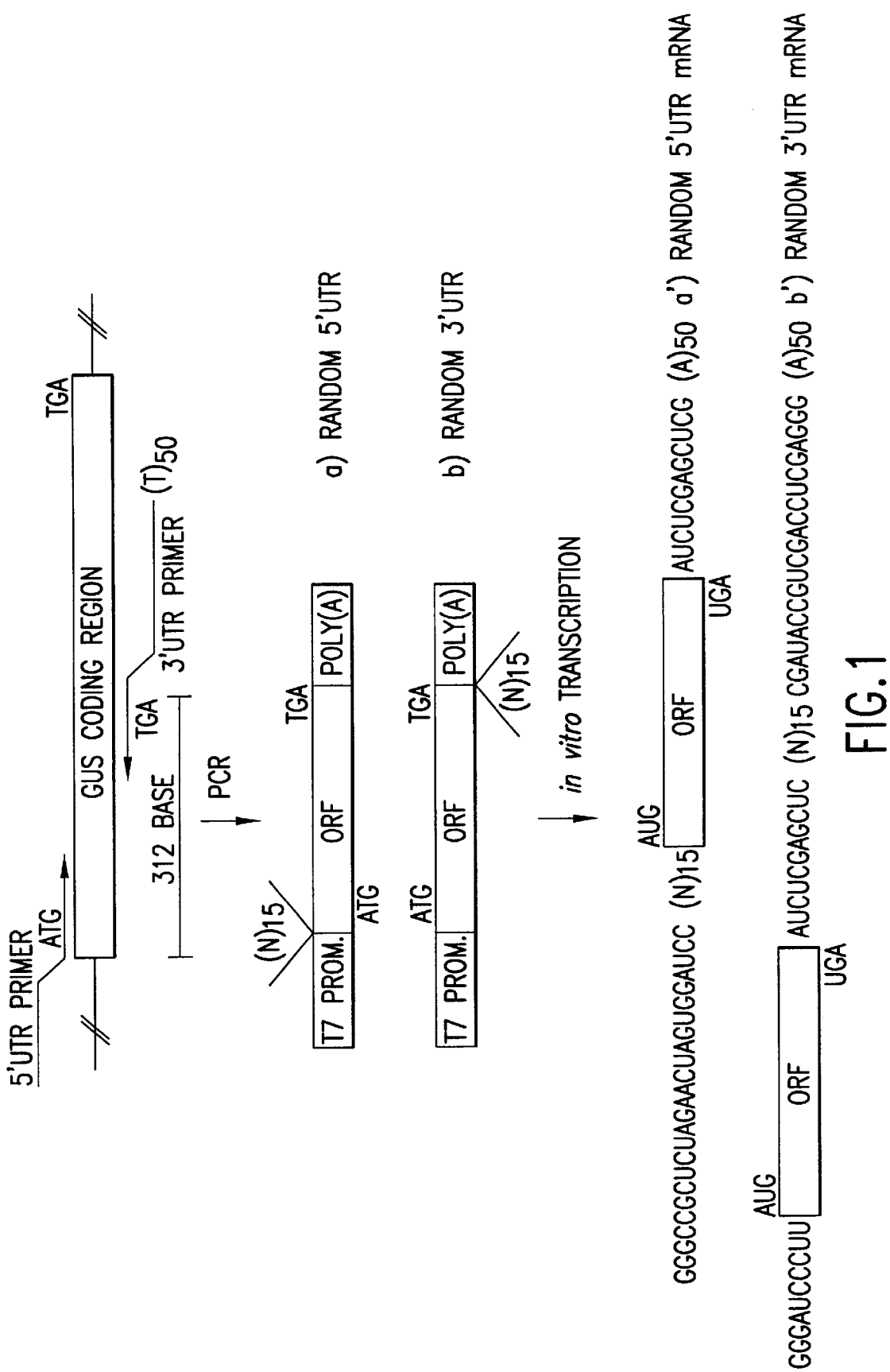
FIG. 1 shows preparation of GUS mRNA having random sequences introduced into the UTR.

First, PCR is performed using 5'-UTR or 3'-UTR primers (where a promoter sequence, e.g. T7, is added to the 5'-end of a forward primer, and a Poly (T) sequence is added to the 5'-end of a reverse primer if necessary) containing a random oligonucleotide sequence and using DNA encoding a protein of interest as a template, thereby preparing two types of double-stranded DNAs (i.e., random 5'-UTR and random 3'-UTR) as shown FIG. 1. Subsequently, in vitro transcription is performed using the two PCR products as templates, so that mRNA with or without Cap corresponding to each of the above double-stranded DNAs is synthesized. Thus, a mRNA population having a random sequence introduced into the 5'-UTR or the 3'-UTR can be prepared by the method, as shown in FIGS. 1a' and b'.

The random oligonucleotide contains 10 or more, preferably 10 to 100, more preferably 15 to 20 nucleotides. Bases selected from adenin (A), thymine (T), guanine (G) and cytosine (C) are located on the random oligonucleotide sequence. When the nucleotide number of an oligonucleotide is n, the obtained DNAs each comprise $4^n$ oligonucleotide sequences.

PCR can be performed under conventional conditions as described in the literature (e.g., Proteins, Nucleic acids & Enzymes, Vol. 41, No. 5, April 1996 (suppl.), Kyoritsu Suppan, Tokyo, Japan; F M. Ausubel et al., Current Protocols in Molecular Biology, John Wiley & Sons, Inc.). For example, PCR is performed for about 25 to about 40 cycles, each of which consists of denaturation of DNA at 94° C. for about 15 to about 30 seconds, and annealing of primers at 55° C. for about 30 seconds to about 1 minute in the presence of a heat-resistant DNA polymerase (e.g., Ampli Taq (Perkin Elmer), Takara Taq (Takara Shuzo Co., Ltd.)), a template DNA and the above-described primers in a water bath or in an automated thermal cycler; and extension reaction at 72° C. for about 30 seconds to about 10 minutes in the co-presence of the four types of substrates (dNTPs); followed by one cycle of the heating treatment at 72° C. for about 5 to about 10 minutes.

The template DNA may be prepared chemically using an automated synthesizer, or by cDNA cloning from an appropriate source, or by isolating from an appropriate cDNA or genomic library. Techniques for cDNA cloning are described in, for example, Sambrook et al., Molecular Cloning, $2^{nd}$ edition, 1989 (Cold Spring Harbor Laboratory Press).

Following preparation of a mRNA population containing various translational regulatory motif (or sequence) candidates in UTR, mRNA with altered translation efficiency in comparison with native mRNA is selected from the mRNA population, thereby identifying a potential translational regulatory sequence. At the first step of this selection, a polysome is synthesized by introducing the mRNA population into an in vitro or in vivo translation system. The in vitro translation system is a so-called cell-free protein synthesis system, which normally comprises use of a cell extract (e.g., an extract from wheat germ, E. coli, or the like) containing elements essential for protein synthesis including ribosome, translation elements, and tRNA (e.g., Madin, K. et al., Proc. Natl. Acad. Sci. USA, 97:559, 2000, Kigawa, T. et al., FEBS Lett., 442: 15, 1999). In the in vitro translation system, polysomes are formed by direct addition of the mRNA population to this system, whereas in the in vivo translation system, eukaryotic cells including frog oocytes are used directly. In this case the mRNA population is introduced into an eukaryotic cell by techniques such as particle gun, micro-injection, and electroporation, followed by culture of the eukaryotic cell in an appropriate medium. Conventional culture conditions may be employed.

Polysome is a single mRNA with multiple ribosomes bound thereto during protein synthesis, and the weight of a polysome differs depending on the number of ribosomes (normally several to several tens of ribosomes). This is because some mRNAs having random sequences in UTR may result in the formation of mRNA populations varying in their translation efficiency. That is, some mRNAs have high translation efficiency or reversely low translation efficiency. When mRNA with high translation efficiency is translated, the so-called large polysome which has many ribosomes bound to the mRNA is formed, whereas when mRNA with low translation efficiency is translated, the so-called small polysome which has few ribosomes bound to the mRNA is formed. Accordingly, the separation of a mRNA population based on the difference in polysome size enables fractionation of mRNA having altered translation efficiency. When a eukaryotic cell is used as the in vivo translation system, then polysome should, prior to the separation, be dissociated from the endplasmic reticulum by, for example, treating with a detergent, because a part of the polysome is bound to the endplasmic reticulum.

Examples of separation techniques include density gradient centrifugation (e.g., sucrose or cesium chloride method), electrophoresis (e.g., capillary electrophoresis), and gel filtration or gel permeation chromatography. In general, mRNA molecules with high translation efficiency bind to a larger number of ribosomes per molecule so that they become distributed on polysome fractions at larger sedimentation rates. On the other hand, mRNA molecules with low translation efficiency become distributed on polysome fractions at smaller sedimentation rates. A mRNA molecule of interest is desirably subjected to the separation process further at least once, preferably twice to 10 times, more preferably 5 to 8 times, since the separation of the mRNAs by a single fractionation is insufficient. In this case, RNA is extracted first from the separated polysome. Next, a DNA fragment is synthesized by reverse transcription (e.g., RT-PCR) using the extracted RNA as a template. Where necessary, a promoter sequence and a poly (T) sequence are further added to the DNA fragment. Then, mRNA is synthesized using the DNA as a template. The mRNA is introduced into an in vitro or in vivo translation system, a polysome of interest is separated, and RNA is separated from the polysome. Then DNA from the RNA and subsequently mRNA from the DNA are synthesized in turn. This cycle is repeated until mRNA of interest is isolated. A mRNA molecule having altered translation efficiency in comparison with the native mRNA is screened by measurement of its translation activity using uptake of $^{35}$S-Cys as described in Example 3 below. Then the potential translational regulatory sequence introduced in the mRNA can be determined by any sequencing method.

The present invention will be further illustrated with reference to the attached drawings. Each step of the methods of this invention will be described using the model gene as an example, which is a modified β-glucuronidase (GUS) gene as a starting gene.

Using the method disclosed by Conrad, R. C. et al (In Smith, C. W. J. ed., RNA: Protein Interactions. A practical Approach. Oxford University Press, New York, pp. 285–325), primers to introduce a random sequence of 15 nucleotides into the 5'-UTR or 3'-UTR of mRNA are designed. A T7 promoter sequence is added on the 5'-terminal side of a forward primer (Lanar, D. E. and Kain, K. C., 1995, Expression-PCR. In Dieffenbach, C. W. and Dveksler, G. S. eds., PCR Primer. A Laboratory Manual.

Cold Spring Harbor Laboratory Press, Cold Spring Harbor, N.Y., pp. 371–377). A termination codon is introduced into a reverse primer so that the first 312 nucleotides of the GUS coding region becomes an ORF, and 50 nucleotides of a poly (T) is added on the 5'-terminal side so that the transcribed mRNA has a poly(A) tract. Next, PCR is performed using these primers, thereby preparing two types of double-stranded DNAs, a random 5'-UTR and a random 3'-UTR, as shown in FIG. 1. Subsequently, in vitro transcription is performed using these two PCR products (i.e., two types of double-stranded DNAs) as templates, thereby synthesizing mRNA having Cap and mRNA having no Cap. Therefore, a mRNA population having random sequences introduced into each of the 5'-UTR and the 3'-UTR is prepared by these procedures (see FIGS. 1a' and b').

Figure 2:
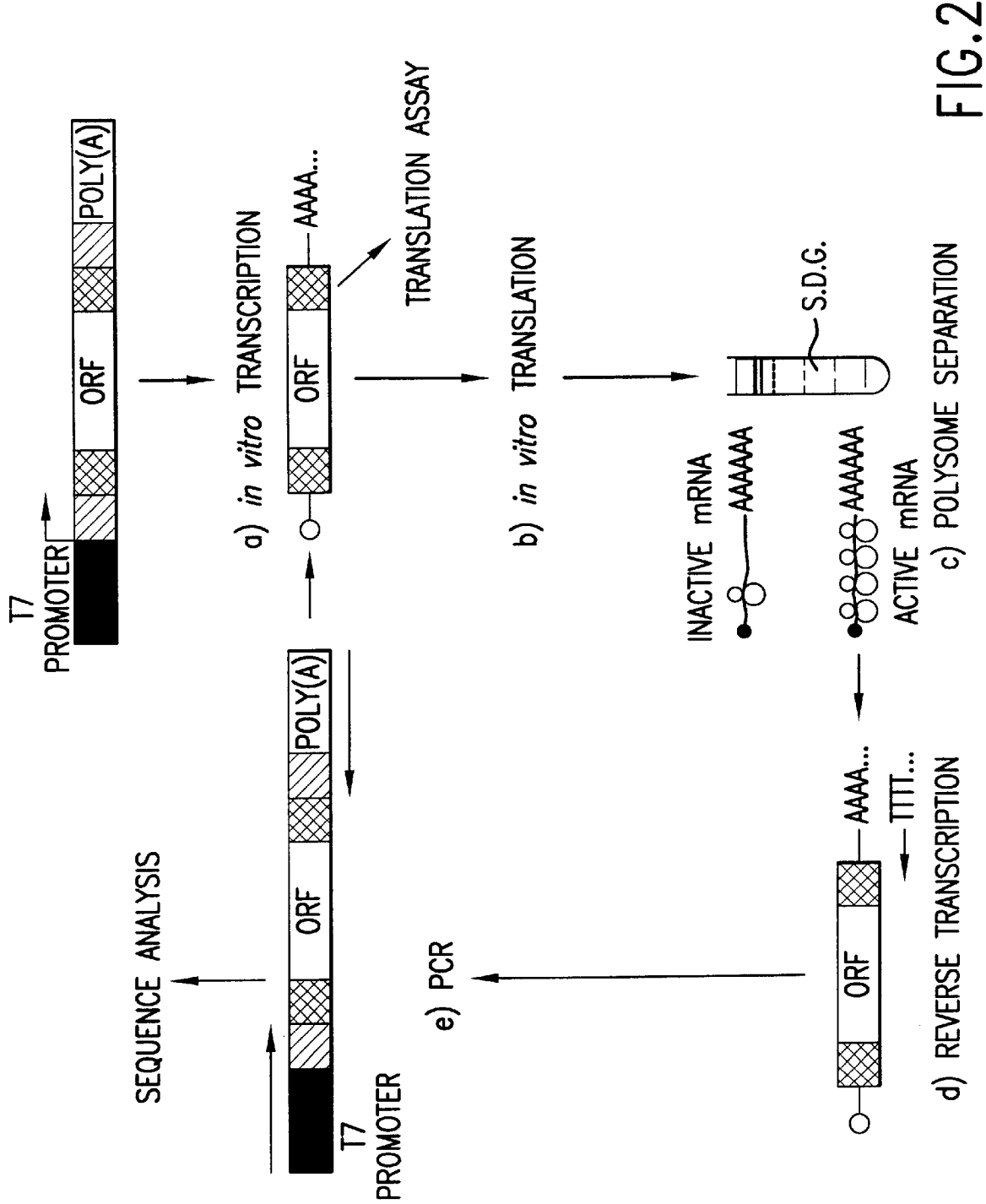
FIG. 2 shows the translation reaction carried out in the wheat germ in vitro translation system. In this figure, the hatched box indicates a random sequence, and the banded box indicates a region to which a PCR primer hybridizes in the second and subsequent cycles.

Translation reaction using a wheat germ in vitro translation system is performed, and polysomes are separated based on the difference in sedimentation coefficient by sucrose density gradient centrifugation (Davis, E. and Abe, S., 1995, In Galbraith, D. W. et al., eds., Methods in Plant Cell Biology, Academic Press, San Diego, pp. 209–222). However, complete separation of mRNA with either high or low translation efficiency may not be achieved by a single round of separation, because a certain degree of fluctuation is present with regards to the binding number of ribosomes even if they bind to the same mRNA molecular species. Accordingly, a series of steps including a separation and fractionation of polysomal RNA, a mRNA synthesis by RT-PCR and an in vitro transcription, a translation reaction, and a re-separation of polysome by sucrose density gradient centrifugation, are repeated several times (FIG. 2). As a result, the present inventors have found that mRNA which has an increased or decreased translation initiation frequency due to introduction of random nucleotide sequences can be enriched in the stepwise manner.

Figure 3A:
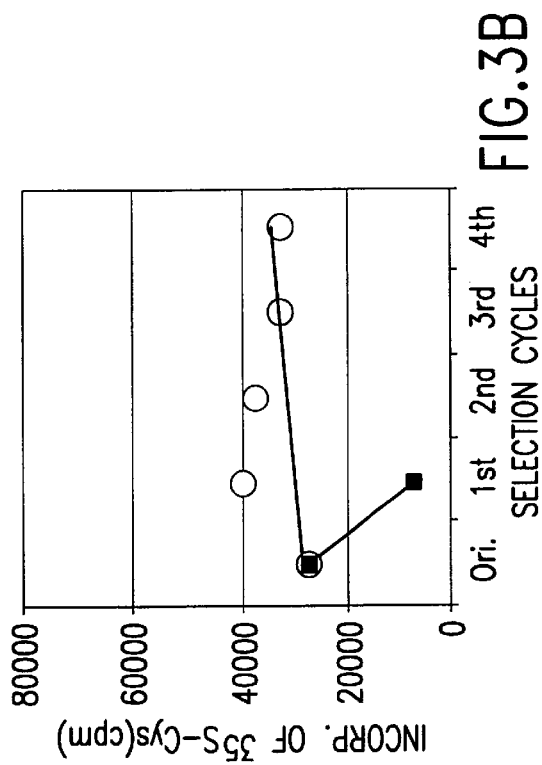
FIG. 3A shows changes in translational activity for a construct obtained by introducing a random sequence into the 5'-UTR of a mRNA having Cap and PolyA strand.
Figure 3B:
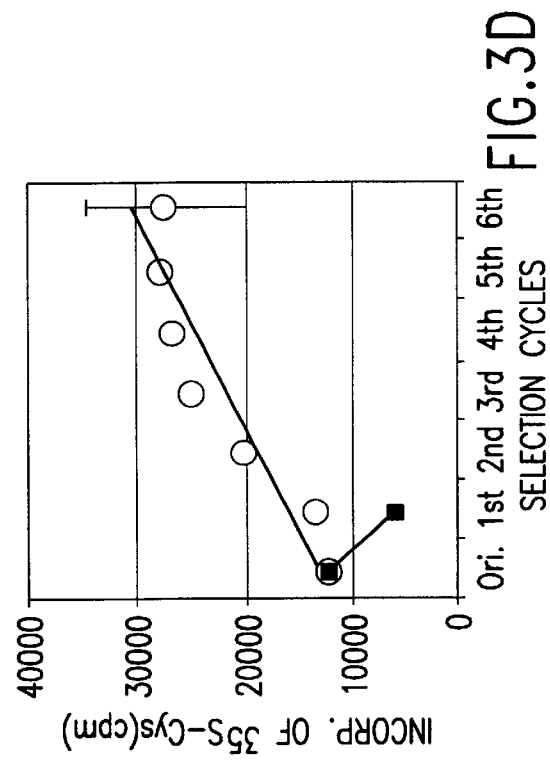
FIG. 3B shows changes in translational activity for a construct obtained by introducing a random sequence into the 3'-UTR of a mRNA having Cap and PolyA strand.

The results of the above-mentioned enrichment cycle using a construct which has Cap, Poly(A), and a random sequence introduced into the 5'-UTR, are shown in FIG. 3A; and the results using a construct which has Cap, Poly(A), and a random sequence introduced into the 3'-UTR, are shown in FIG. 3B. The translation activity approximately three-fold greater than that of the initial population was found for the 5'-UTR, while no increase in the activity was found for the 3'-UTR. Thus, the mRNA population with the increased translation activity was separated. In low activity fractions for both the constructs, mRNA populations with the activity decreased to approximately 25% were separated. There is an approximately 10-fold difference in the activity between the high and the low activity populations. These results suggest that, in mRNA having Cap and Poly(A), the 5'-UTR mainly functions as a sequence for promoting translation.

A Cap structure is known to play an important role in the translational initiation reaction in eukaryotic organisms (Gingras, A. C. et al., 1999, Annu. Rev. Biochem., 68: 913–963). Moreover, many RNA viruses are known to disrupt the Cap-dependent translational initiation apparatus in a host cell by their specific proteinases so that their own mRNA that takes the Cap-independent translational initiation mechanism can preferentially be translated (Ehrenfeld, E., 1996: In Hershey, J. W. B et al., eds., Translational Control, Cold Spring Harbor Laboratory Press, Cold Spring Harbor, N.Y., pp. 549–573). To examine by the method of this invention how the cap structure affects the expression of a translational regulatory element, a random sequence is introduced into the 5'-UTR or the 3'-UTR of Poly(A) mRNA without Cap followed by the experiment as described above (FIGS. 3C and 3D). As a result, an approximately 3-fold increase was found in the translation activity of the mRNA having a random sequence introduced into the 3'-UTR. In the low activity population, its activity declines to approximately 50%, which is approximately one sixth of that of the high activity having population.

The above-mentioned results suggest that Cap and Poly (A) are required for a translational regulatory sequence on the 5'-UTR to sufficiently exert its function, and a translation-promoting sequence, which can compensate for deletion of Cap, is allowed to appear in a sequence on the 3'-UTR. Particularly the fact that Cap-independent translation-promoting sequence appears on the 3'-UTR is very surprising because the position (5'-terminus) where the 5' cap should be located is distant from the 3'-UTR.

Figure 4A:
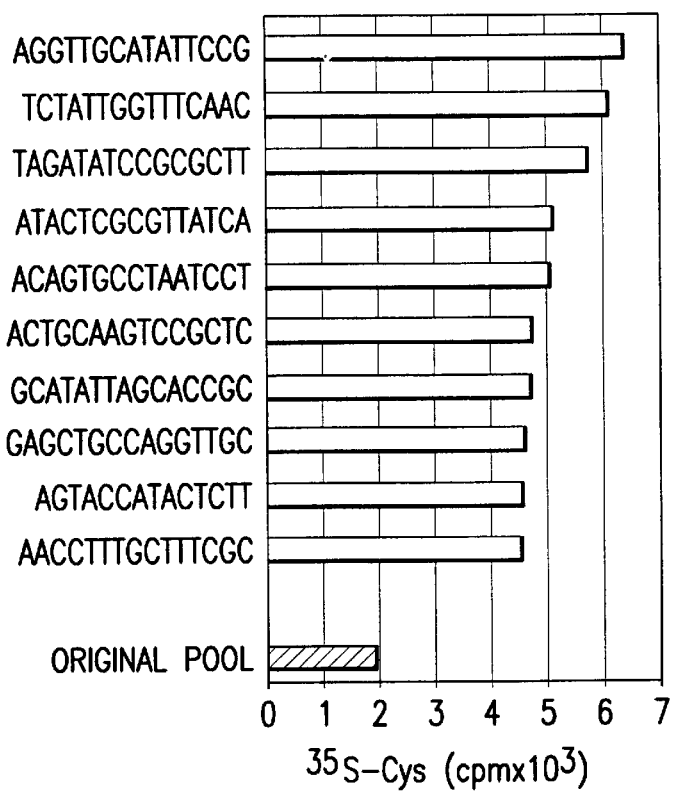
FIG. 4A shows those of constructs obtained by introducing random sequences into the 5'-UTR of a mRNA having Cap and PolyA strand.
Figure 4B:
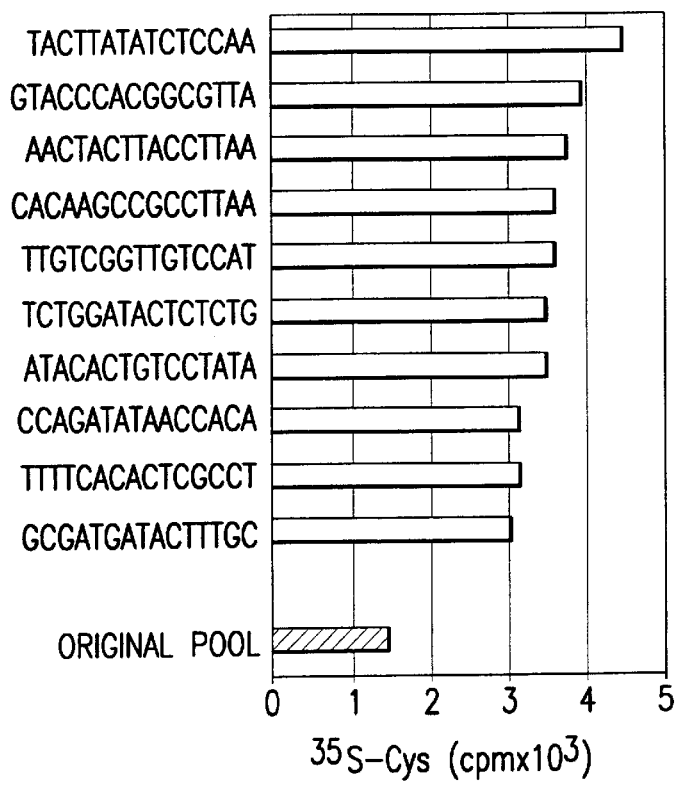
FIG. 4B shows those of constructs obtained by introducing random sequences into the 3'-UTR of a mRNA having PolyA strand but no Cap.

Next, cloning of each cDNA from the resulting high translation activity-possessing mRNA populations is performed for two examples, by which mRNA populations with increased translation activity are obtained; the one example in which a random sequence has been introduced into the 5'-UTR of mRNA having Cap, and the other in which a random sequence has been introduced into the 3'-UTR of mRNA without Cap. FIG. 4 shows the sequences of the random regions of the cloned constructs, and the results of measurement on the translation activities of the clones. Examples of potential translational regulatory sequences with increased translation activity are as shown below (see FIG. 4A and FIG. 4B).

Random sequences introduced into the 5' UTR are as follow:

| | |
|---|---|
| AGGUUGCAUAUUCCG | (SEQ ID NO: 9) |
| UCUAUUGGUUUCAAC | (SEQ ID NO: 10) |
| UAGAUAUCCGCGCUU | (SEQ ID NO: 11) |
| AUACUCGCGUUAUCA | (SEQ ID NO: 12) |
| ACAGUGCCUAAUCCU | (SEQ ID NO: 13) |
| ACUGCAAGUCCGCUC | (SEQ ID NO: 14) |
| GCAUAUUAGCACCGC | (SEQ ID NO: 15) |
| GAGCUGCCAGGUUGC | (SEQ ID NO: 16) |
| AGUACCAUACUCUU | (SEQ ID NO; 17) |
| AACCUUUGCUUUCGC | (SEQ ID NO: 18) |

Random sequences introduced into 3'UTR are as follows:

| | |
|---|---|
| UACUUAUAUCUCCAA | (SEQ ID NO: 19) |
| GUACCCACGGCGUUA | (SEQ ID NO: 20) |
| AACUACUUACCUUAA | (SEQ ID NO: 21) |
| CACAAGCCGCCUUAA | (SEQ ID NO: 22) |
| UUGUCGGUUGUCCAU | (SEQ ID NO: 23) |
| UCUGGAUACUCUCUG | (SEQ ID NO: 24) |
| AUACACUGUCCUAUA | (SEQ ID NO: 25) |
| CCAGAUAUAACCACA | (SEQ ID NO: 26) |
| UUUUCACACUCGCCU | (SEQ ID NO: 27) |
| GCGAUGAUACUUUGC | (SEQ ID NO: 28) |

Prima facie, the clone sequences obtained from the isolated high activity having populations have no common properties, suggesting the presence of multiple UTR sequences involved in promoting the mRNA translation.

When a binding sequence of a nucleic acid-binding protein is screened by the in vitro evolution, it often converges into a certain sequence (Szoztak, J. W., 1992, Trends in Biochemical Sciences, 17: 89–93). However in the translation reaction, which is a very complex biochemical reaction, various factors may affect the screening of a UTR translational regulatory sequence. Any of the proteins and RNA involved in the translation reaction may possibly affect the screening. The likely reason why a certain sequence is not detected is that various control mechanisms associated with many factors are involved in the screening of UTR sequences.

The present invention will be further described by the following examples, but the invention is not limited by these examples.

EXAMPLES

Example 1

Preparation of GUS mRNA Having Random Sequences Introduced in UTR

PCR was performed using a combination of the following forward and reverse primers to introduce random sequences into the 5' UTR or the 3' UTR of GUS gene, thereby preparing double-stranded DNA fragments as shown in FIG. 1 (Lanar and Kain, supra).

Forward and reverse primers:

in vitro translation system (Promega) containing the whole amino acids (FIG. 2, step b). Following reaction, ice-cooled 100 μl of U-Buffer (200 mM Tris-HCl, pH 8.5, 50 mM KCl, 25 mM $MgCl_2$, 2 mM EDTA, 100 μg/ml heparin, 2% polyoxyethylene 10-tridecyl ether, 1% sodium deoxycholate) was added to stop the reaction. The reaction solution 160 μl was applied to a tube containing a solution with sucrose density gradient (50 mM Tis-HCl, pH 8.5, 25 mM KCl, 10 mM $MgCl_2$, 15–60% sucrose) followed by centrifugation at 125000 rpm for 3 hours (Davis and Abe, supra). Following centrifugation, products were fractionated into 12 fractions, approximately 1 ml each, using a fraction collector (FIG. 2, step c). Next, RNA was collected from these fractions, and then double-stranded DNA was prepared by SUPERSCRIPT™ ONE-STEP™ RT-PCR System (GIBCO BRL) (FIG. 2, step e). Here, a forward primer 5'-GCAGGCCTAATACGACTCACTATAGGGCCGCTC TAGAACTAGTGGATC-3' (SEQ ID NO: 6) and a reverse primer (SEQ ID NO: 2) were used for mRNA having a random sequence in the 5'UTR. A forward primer (SEQ ID NO: 3) and a reverse primer (SEQ ID NO: 5) were used for mRNA having a random sequence in the 3'UTR. Subsequently, in vitro transcription was performed using these fragments to prepare mRNA again (FIG. 2, step a), followed by repeating a cycle as shown with bold lines in FIG. 2. In the third and subsequent enrichment cycles, the translation reaction was performed in the presence of an added competitive RNA molecule.

A modified fire fly luciferase gene was used as the competitive mRNA. mRNA with Cap was used as the

```
(1) 5'-GCAGGCCTAATACGACTCACTATAGGGCGGCTCTAGAACTAGTGGATCC-    (SEQ ID NO: 1)
(N)₁₅ATGTTACGTCCTGTAGAAACCCCAACCCGT-3'

(2) 5'-(T)₅₀CGAGCTCGAGATTCACACTTCCTGATTATTGACCCACACT-3'       (SEQ ID NO: 2)

(3) 5'-GCCTGCAGGGCCTAATACGACTCACTATAGGGATCCCTTATGTTACGTCC     (SEQ ID NO: 3)
TGTAGAAACCCCA-3'

(4) 5'-CCCTCGAGGTCGACGGTATCG-(N)₁₅GAGCTCGAGATTCACACTTCCTGA    (SEQ ID NO: 4)
TTATTGA-3'

(5) 5'-(T)₅₀CCCTCGAGGTCGACGGTATCG-3'                          (SEQ ID NO: 5)
```

Constructs having random sequences in the 3'UTR were prepared using primers (3) and (4) first. PCR was performed using the fragments as templates and primers (3) and (5), thereby adding a Poly(A) tail. In vitro transcription was performed for preparing mRNA with Cap using a mMESSAGE mMACHINE T7 Kit (Ambion, containing Cap analog in the reaction solution), and for preparing mRNA competitive mRNA for screening mRNA with Cap; mRNA without Cap was used as the competitive mRNA for screening mRNA without Cap. The following two primers (SEQ ID NOS: 7 and 8) were designed as in the method described in FIG. 1, so that the first 321 nucleotides become the ORF.

Two primers (SEQ ID NOS: 7 and 8):

```
5'-GCAGGCCTAATACGACTCACTATAGGGATCCAAATGGAAGACGCCAAAAA    (SEQ ID NO:7)
CATAAAGAA-3'

5'-(T)₅₀CGAGCTCGAGATTTTAGTTCGCGGGCGCAACTGCAACTCCGAT-3'   (SEQ ID NO:8)
``` without Cap using a Mega Script T7 Kit (Ambion, containing no Cap analog in the reaction solution). Thus, mRNA having random sequences in the 5'UTR or the 3'UTR were prepared.

Example 2

Translation Reaction in a Wheat Germ In Vitro Translation System mRNA shown in FIG. 1 was translated with an active fraction of mRNA for 10 minutes, and with an inert fraction of mRNA for 30 minutes at 25° C. in 100 μl of a wheat germ PCR was performed using these primers, thereby obtaining DNA fragments as templates.

Example 3

Changes in Translation Activity Associated with Enrichment Cycle

Enrichment cycle was performed using constructs having random sequences in the 5' UTR of mRNA with Cap and Poly(A) strand, and then changes in translation activity with the cycle were measured. FIG. 3A shows the results. In this Figure, the translation activity measured with uptake of $^{35}$S-Cys was plotted on the ordinate, and the number of enrichment cycles on the abscissa. Translation activity was measured using a wheat germ translation system containing 20 µl of $^{35}$S-Cys. Following the reaction at 25° C. for 60 minutes, the reaction solution was dispensed in an amount of 2 µl in a tube containing 98 µl of 1N NaOH. The solution was maintained at 37° C. for 10 minutes, added with 900 µl of 25% TCA/2% casamino acid, and then cooled for 1 hour at 4° C. After centrifugation at 15,000 rpm for 5 minutes, the supernatant was discarded, and then the product was rinsed with 5% TCA. Liquid scintillator 200 µl was added to the tube, followed by measurement of radioactivity using a liquid scintillator counter (Herwynen, J. F. V. and Beckler, G. S., 1995: In Tymms, M. J., ed., In Vitro Transcription and Translation Protocols, Humana Press, Totowa, N.J., Vol. 37, pp. 245–251).

Figure 3C:
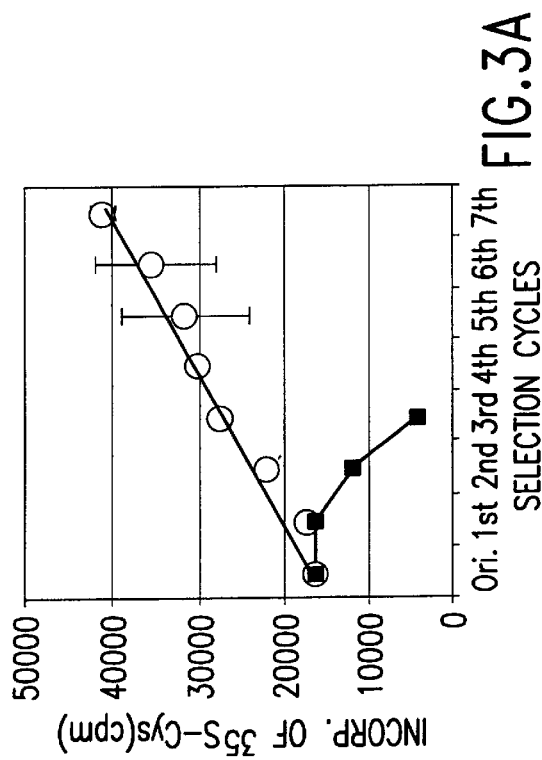
FIG. 3C shows changes in translational activity for a construct obtained by introducing a random sequence into the 5'-UTR of a mRNA having PolyA strand but having no Cap.
Figure 3D:
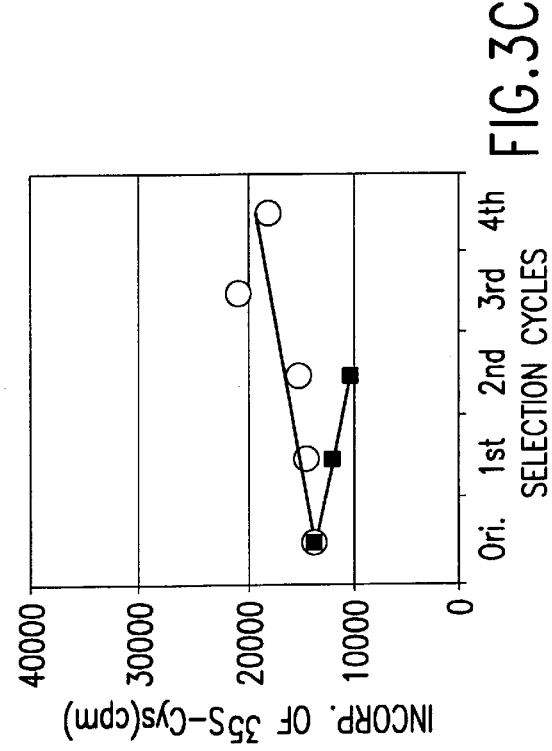
FIG. 3D shows the change for a construct obtained by introducing a random sequence into the 3'UTR of an mRNA having PolyA strand but having no Cap. The open circle indicates a construct whose translational activity was high or showed almost no change; and the solid square indicates a construct whose translational activity was low.

FIG. 3B shows the results obtained for the construct having a random sequence introduced in the 3'UTR of the mRNA without Cap and Poly(A) strand, FIG. 3C shows the results obtained for the construct having a random sequence introduced in the 5'UTR of mRNA with Poly(A) strand but with no Cap, and FIG. 3D shows the results obtained for the construct having a random sequence introduced in the 3'UTR of mRNA with Poly(A) but without Cap.

For the mRNA having a Cap structure, a mRNA population having increased translation activity in the 5' UTR an approximately 3-fold greater than that of the initial population was isolated, while no increased activity was found in the 3'UTR (in comparison of FIG. 3A with FIG. 3B). For the mRNA having no Cap structure, an approximately 3-fold increase in translation activity was observed in the mRNA having a random sequence introduced in the 3'UTR (comparison of FIG. 3C with FIG. 3D).

Example 4

Sequences and Translation Activity of mRNA Population With Promoted Translation

The translation-promoting sequence was sequenced, and the translation activity was measured for a high activity population obtained from the constructst having a random sequence introduced into the 5'UTR of mRNA with Cap and Poly(A) strand (FIG. 4A). Moreover, the translation-promoting factor sequence was sequenced, and the translation activity was measured for a high activity population obtained from the constructst having a random sequence introduced into the 3'UTR of mRNA with Poly(A) strand but without Cap (FIG. 4B). Activity was measured as described in Example 3.

Prima facie, the clone sequences obtained from the high activity populations isolated have no properties in common, suggesting the presence of multiple UTR sequences involved in promoting mRNA translation.

ADVANTAGES OF THE INVENTION

The advent of a new control mechanism mediated by a sequence generated by in vitro evolution is similar to the way viruses have acquired their own unique gene expression control mechanism to proliferate in host cells. From such a stand point, a comprehensive and systematic analysis of translation controlling sequences according to the present invention may be useful for preventive studies against pathogenic viruses which may emerge in the future.

Controlling translation efficiency and gene expression by 5' UTR and 3' UTR to regulate expression amount without altering protein function is one evolutionally effective measure. Experiments conducted for UTR regulating sequences known as translation enhancers or translation repressors, wherein for example a reporter gene is introduced into UTR of another gene, are known to produce various results including largely varying degrees of effect, no effect, or the opposite effect. This may be caused by the flexible structure of single-stranded mRNA. That is, an altered nucleotide sequence resulted in similarly altered stereostructure derived from interaction of intramolecular bases. The present invention enables a sequence that surely increases or decreases the translation activity of mRNA regardless of the stereostructure or intramolecular interaction of the mRNA to be obtained. Therefore, the present invention exploits a new technological field to artificially and surely control expression of a targeted gene during translation.

Application of the present invention to an in vivo translation system is expected to give specific translational control to mRNA of a gene of interest under an environment with a variety of external stimulation including light, hormones, and tissue-specific expression in plant tissues, and tissues, developmental differentiation processes, and hormones in animal cells, and to enable artificial gene control.

What is claimed is:

1. A method of screening a potential translational regulatory element of mRNA, comprising the steps of synthesizing mRNAs containing random oligonucleotide sequences, which are candidates of translational regulatory elements, introduced into untranslated regions (UTRs), and selecting mRNA with altered translation efficiency by virtue of the inserted motifs, wherein said mRNA is selected by: (a) introducing an mRNA population, which contains various translational regulatory motif candidates in the UTRs, into an in vitro or in vivo translation system to produce polysomes; and (b) separating a polysomal mRNA with altered translation efficiency.

2. The method of claim 1, further comprising the steps of: (c) extracting RNA from said separated polysomes; and (d) synthesizing a DNA fragment using the RNA as a template, then synthesizing mRNA using the DNA fragment as a template.

3. The method of claim 2, further comprising the steps of: (e) repeating at least once said steps (a) to (d) for said synthesized mRNA to isolate substantially pure mRNA with altered translation efficiency; and (f) determining a sequence of a potential translational regulatory element introduced into the isolated mRNA.

4. The method of claim 1 wherein said synthesized mRNA contains either of a Cap structure or a Poly(A) strand, or both.

5. The method of claim 1 wherein said in vitro translation system is a cell-free protein synthesis system, and said in vivo translation system is an eukaryotic cell.

6. The method of claim 1 wherein said separation of a polysomal mRNA in said step (b) is performed based on size.

7. The method of claim 1 wherein said mRNA with altered translation efficiency has a higher or lower translation efficiency than that of native mRNA.

8. A method of screening a potential translational regulatory element of mRNA, comprising the steps of:
(a) synthesizing mRNAs containing random oligonucleotide sequences, which are candidates of translational regulatory elements, introduced into either or both of the 5'-untranslated region (5'-UTR) and the 3'-untranslated region (3'-UTR), and containing a Cap structure and a Poly (A) strand sequence;
(b) introducing the mRNA population synthesized in step (a), which contains various translational regulatory motif candidates in the 5'-UTR and/or 3'-UTR, into an in vitro or in vivo translation system to produce polysomes;
(c) separating, based on size, a polysome containing the mRNA which has a translation efficiency higher than that of the native mRNA
(d) extracting RNA from the polysome separated in the step (c);
(e) synthesizing a DNA fragment using the RNA extracted in step (d) as a template, then synthesizing mRNA using the DNA fragment as a template;
(f) repeating at least once the steps (b) to (e) for the mRNA obtained in the step (e), and then isolating substantially pure mRNA with translation efficiency higher or lower than that of the native mRNA; and
(g) determining a sequence of a potential translational regulatory element introduced in the mRNA isolated in step (f).

9. A method of screening a potential translational regulatory element of mRNA, comprising the steps of:
(a) synthesizing mRNAs containing random oligonucleotide sequences, which are candidates of translational regulatory elements, introduced into either or both of the 5'-untranslated region (5'-UTR) and the 3'-untranslated region (3'-UTR), and containing no Cap structure but containing a Poly (A) strand sequence;
(b) introducing the mRNA population synthesized in step (a), which contains various translational regulatory motif candidates in the 5'-UTR and/or 3'-UTR, into an in vitro or in vivo translation system to produce polysomes;
(c) separating, based on size, a polysome containing the mRNA which has a translation efficiency higher than that of the native mRNA;
(d) extracting RNA from the polysome separated in the step (c);
(e) synthesizing a DNA fragment using the RNA extracted in step (d) as a template, then synthesizing mRNA using the DNA fragment as a template;
(f) repeating at least once the steps (b) to (e) for the mRNA obtained in the step (e), and then isolating substantially pure mRNA with translation efficiency higher or lower than that of the native mRNA; and (g) determining a sequence of a potential translational regulatory element introduced in the mRNA isolated in step (f).

10. A method of screening a translational regulatory element of a native mRNA with high translation efficiency, comprising the steps of:
   (a) introducing a mRNA population, which contains various translational regulatory motifs in either or both of the 5'-untranslated regions and the 3-untranslated regions (3'-UTR), into an in vitro or in vivo translation system to produce polysomes;
   (b) separating, based on size, a polysome containing the mRNA which has a high translation efficiency;
   (c) extracting RNA from the polysome separated in the step (b);
   (d) synthesizing a DNA fragment using the RNA extracted in step (c) as a template, then synthesizing mRNA using the DNA fragment as a template;
   (e) repeating at least once the steps (a) to (d) for the mRNA obtained in the step (d),
   and then isolating substantially pure mRNA with high translation efficiency; and
   (f) determining a sequence of a potential translational regulatory element of the mLRNA isolated in step (e).

11. A method of screening a potential translational regulatory element of mRNA, comprising the steps of:
   (a) synthesizing mRNAs containing random oligonucleotide sequences, which are candidates of translational regulatory elements, introduced into the untranslated regions (UTRs);
   (b) introducing the mRNA population synthesized in step (a), which contains various translational regulatory motif candidates in the UTRs into an in vitro or in vivo translation system to produce polysomes;
   (c) separating, based on size, a polysome containing the mRNA which has an altered translation efficiency;
   (d) extracting RNA from the polysome separated in the step (c);
   (e) synthesizing a DNA fragment using the RNA extracted in step (d) as a template, then synthesizing mRNA using the DNA fragment as a template;
   (f) repeating at least once the steps (b) to (e) for the mRNA obtained in the step (e), and then isolating substantially pure mRNA with altered translation efficiency; and
   (g) determining a sequence of a potential translational regulatory elements introduced in the mRNA isolated in step (f).

12. A method of screening a potential translational regulatory element of comprising the steps of:
   (a) synthesizing mRNAs containing random oligonucleotide sequences, which are candidates of translational regulatory elements, introduced into either or both of the 5'-untranslated region (5'-UTR) and/or the 3'-untranslated region (3'-UTR), and containing a CAP structure but no Poly (A) strand sequence;
   (b) introducing the mRNA population synthesized in step (a), which contains various translational regulatory motif candidates in the 5'-UTR and/or 3'-UTR, into an in vitro or in vivo translation system to produce polysomes;
   (c) separating, based on size, a polysome containing the mRNA which has a translation efficiency higher than the native mRNA;
   (d) extracting RNA from the polysome separated in the step (c);
   (e) synthesizing a DNA fragment using the RNA extracted in step (d) as a template, then synthesizing mRNA using the DNA fragment as a template;
   (f) repeating at least once the steps (b) to (e) for the mRNA obtained in the step (e), and then isolating substantially pure mRNA with altered translation efficiency; and
   (g) determining a sequence of a potential translational regulatory elements introduced in the mRNA isolated in step (f).

* * * * *